United States Patent
Redel

(10) Patent No.: US 10,555,712 B2
(45) Date of Patent: Feb. 11, 2020

(54) SEGMENTING AN ANGIOGRAPHY USING AN EXISTING THREE-DIMENSIONAL RECONSTRUCTION

(71) Applicant: Thomas Redel, Poxdorf (DE)

(72) Inventor: Thomas Redel, Poxdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 62 days.

(21) Appl. No.: 15/687,272

(22) Filed: Aug. 25, 2017

(65) Prior Publication Data

US 2018/0055471 A1    Mar. 1, 2018

(30) Foreign Application Priority Data

Aug. 25, 2016 (DE) .......... 10 2016 215 971

(51) Int. Cl.
*A61B 6/00* (2006.01)
*G06T 7/11* (2017.01)
(Continued)

(52) U.S. Cl.
CPC .............. *A61B 6/504* (2013.01); *A61B 5/055* (2013.01); *A61B 6/5229* (2013.01); *A61B 6/5276* (2013.01); *G06T 7/0012* (2013.01); *G06T 7/11* (2017.01); *G06T 7/174* (2017.01); *G06T 7/30* (2017.01); *G06T 11/003* (2013.01); *A61B 6/032* (2013.01); *A61B 6/5223* (2013.01); *G06T 2207/10081* (2013.01); *G06T 2207/10088* (2013.01); *G06T 2207/30048* (2013.01);
(Continued)

(58) Field of Classification Search
None
See application file for complete search history.

(56) References Cited

U.S. PATENT DOCUMENTS 6,148,095 A * 11/2000 Prause .............. G06T 17/00
128/916
9,814,433 B2 * 11/2017 Benishti ............ G16H 50/30
(Continued)

FOREIGN PATENT DOCUMENTS

DE    602004002939 T2    6/2007

OTHER PUBLICATIONS

Markelj, Primoz, et al. "A review of 3D/2D registration methods for image-guided interventions." Medical image analysis 16.3 (2012): 642-661. (Year: 2012).*

(Continued)

*Primary Examiner* — Samah A Beg
(74) *Attorney, Agent, or Firm* — Lempia Summerfield Katz LLC

(57) ABSTRACT

A method for segmenting a two-dimensional angiographic recording of a vessel of a body using a computing apparatus includes providing a three-dimensional reconstruction of the vessel of the body to the computing apparatus. The two-dimensional angiographic recording of the vessel of the body is provided on the computing apparatus. The three-dimensional reconstruction of the vessel of the body is registered with the two-dimensional recording of the vessel of the body. Spatial information of the three-dimensional reconstruction is projected onto the two-dimensional recording, and the two-dimensional recording is segmented using the spatial information projected onto the two-dimensional recording.

19 Claims, 1 Drawing Sheet

(51) Int. Cl.
*G06T 7/30* (2017.01)
*G06T 7/174* (2017.01)
*A61B 5/055* (2006.01)
*G06T 7/00* (2017.01)
*G06T 11/00* (2006.01)
*A61B 6/03* (2006.01)

(52) U.S. Cl.
CPC ............... *G06T 2207/30104* (2013.01); *G06T 2211/404* (2013.01)

(56) References Cited

U.S. PATENT DOCUMENTS

| | | | |
|---|---|---|---|
| 2006/0036167 A1* | 2/2006 | Shina | A61B 6/12 600/433 |
| 2006/0159326 A1* | 7/2006 | Rasche | G06T 11/008 382/131 |
| 2008/0037843 A1* | 2/2008 | Fu | G06T 15/08 382/128 |
| 2008/0212857 A1* | 9/2008 | Pfister | A61B 5/02007 382/130 |
| 2009/0005668 A1* | 1/2009 | West | A61B 6/466 600/407 |
| 2009/0052757 A1* | 2/2009 | Khamene | A61B 6/5235 382/131 |
| 2010/0310140 A1* | 12/2010 | Schneider | G06K 9/6247 382/130 |
| 2011/0069063 A1* | 3/2011 | Liao | A61B 6/5235 345/419 |
| 2012/0323547 A1* | 12/2012 | Baloch | G16H 50/50 703/11 |
| 2013/0070995 A1* | 3/2013 | Chou | G06T 7/344 382/131 |
| 2014/0270436 A1* | 9/2014 | Dascal | G06T 7/11 382/130 |
| 2015/0131886 A1* | 5/2015 | Aben | A61B 6/12 382/132 |
| 2015/0178886 A1* | 6/2015 | Pfister | G06T 5/50 382/132 |
| 2015/0302578 A1 | 10/2015 | Grady et al. | |
| 2017/0039736 A1* | 2/2017 | Aben | G06T 11/003 |
| 2018/0150960 A1* | 5/2018 | Derda | G06T 7/11 |
| 2019/0019347 A1* | 1/2019 | Auvray | G06T 19/20 |

OTHER PUBLICATIONS

Mitrovic, Uros, et al. "3D-2D Registration of Cerebral Angiograms: A Method and Evaluation on Clinical Images." IEEE Transactions on Medical Imaging 8.32 (2013): 1550-1563. (Year: 2013).*

Sundar, Hari, et al. "A novel 2D-3D registration algorithm for aligning fluoro images with 3D pre-op CT/MR images." Medical Imaging 2006: Visualization, Image-Guided Procedures, and Display. vol. 6141. International Society for Optics and Photonics, 2006. (Year: 2006).*

Morris, Paul D., et al. ""Virtual" (computed) fractional flow reserve: current challenges and limitations." JACC: Cardiovascular Interventions 8.8 (2015): 1009-1017.

* cited by examiner

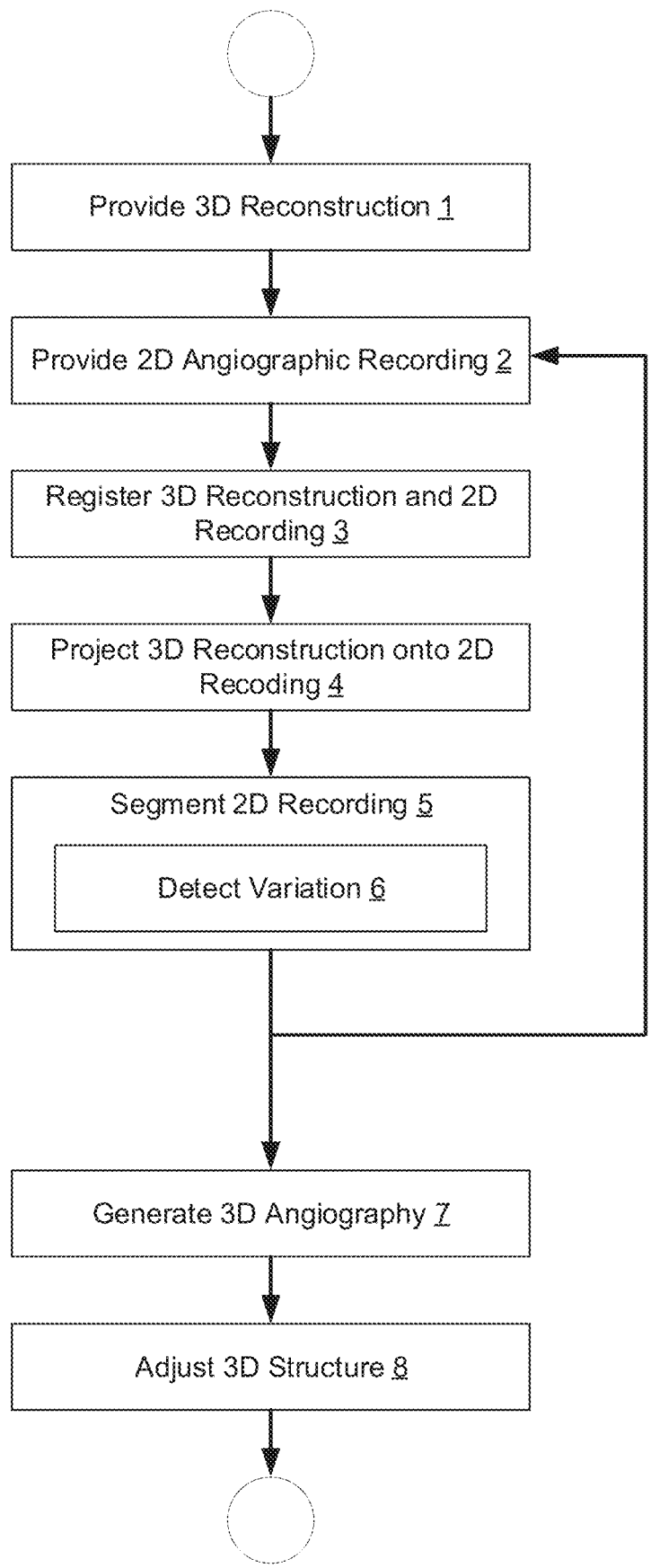

SEGMENTING AN ANGIOGRAPHY USING AN EXISTING THREE-DIMENSIONAL RECONSTRUCTION

This application claims the benefit of DE 10 2016 215 971.2, filed on Aug. 25, 2016, which is hereby incorporated by reference in its entirety.

BACKGROUND

The present embodiments relate to segmenting a two-dimensional angiographic recording of a vessel of a body.

One established clinical characteristic is the fractional flow reserve (FFR), which may be measured with a compression wire, for example. In such cases, the compression wire is guided past a stenosis in the vessel or vascular segment of the body, and the pressure is determined there distally in relation to the stenosis. This distal pressure is divided by the proximal pressure in order to calculate the fractional flow reserve.

It is possible to calculate the pressure course across the stenosis using mathematical fluid dynamics methods (e.g., computational fluid dynamics). It is also possible to virtually calculate a virtual value for the fractional flow reserve, a virtual FFR value, based on the three-dimensional model using a three-dimensional model of the vascular segment of the body that contains the stenosis. Further boundary conditions such as, for example, the blood flow in milliliters per second through the vascular segment of the body may also be calculated. Methods of this type are known and described, for example, in the article by Paul D. Morris et al.: "''Virtual'' (Computed) Fractional Flow Reserve—Current Challenges and Limitations" in JACC: Cardiovascular Interventions, Vol. 8, No. 8, 2015, pages 1009 to 1117. Further calculation methods for a virtual FFR value are also known.

The approaches to virtual calculation of the fractional flow reserve may be divided into two groups: Non-invasive methods, in which geometric information relating to the vascular segment or vessel of the body is obtained by computed tomography, magnetic resonance tomography, or other methods; and minimally invasive methods, in which the geometric information is obtained with a subsequent x-ray recording in the heart catheter laboratory by injecting contrast agent into the vessel. A non-invasive examination is firstly carried out on a patient using computed tomography (CT). Aside from the diagnostic information relating to one or a number of vascular cross-sections of the examined vascular segment or vessel of the body, in such cases, a virtual value may also be calculated for the fractional flow reserve (e.g., CT-FFR value). In contrast, a virtual value for a fractional flow reserve, which is determined by angiography in the heart catheter laboratory, for example, is referred to below as angio-FFR value.

The CT-FFR method (e.g., the calculation of the virtual FFR value using a CT) is advantageous in that a three-dimensional model of the entire vascular tree, in which the vessel of the body or the vascular segment of the body with the stenosis is located, is available. The CT-FFR method also permits a good determination of the perfused myocardial mass and of the perfusion flow derived from the portion of the perfused myocardial mass. Additional information such as, for example, a combining of the stenosis or plaque may also be determined. The disadvantage is the comparably minimal spatial resolution and thus an inaccurate geometrical representation of the stenosis geometry.

By comparison, the angio-FFR method (e.g., the calculation of a virtual FFR value via an angiography) has the advantage of a good spatial resolution that allows for an accurate representation of the stenosis geometry. The disadvantage is the estimation of the blood through the vascular cross-sections. Small errors may already have significant repercussions. Estimating the blood flow via the contrast agent dynamics with the angio-FFR method is also complicated and difficult. It is also disadvantageous that the angio-FFR method provides no information relating to a state of the myocardial mass, which is important, for example, in order to identify possible initial damages so as to be able to take these into account during a treatment, for example. Geometric information of the entire vascular tree may only be achieved with extreme difficulty; this also relates back to the relatively small detectors that are typically used in angiographies.

To calculate an FFR value with the angio-FFR method, a segmentation of the two-dimensional recordings or angiography images and subsequently typically a generation of a three-dimensional angiography including at least two two-dimensional recordings may be provided. A recording or x-ray recording is also described here as an acquisition or angiography scene. The data contained in a recording may represent a film with a plurality of individual images at a generally fixed or non-variable predetermined angulation (e.g., a predetermined recording angle that is non-variable relative to the recorded vessel of the body for the acquisition or recording). In particular acquisitions, the individual images contained in a recording may be recorded at different angulations. In this case, the precise assignment of the individual images with the corresponding angulation is, however, required or provided.

A segmentation of the relevant vessel of the body into the at least two two-dimensional recordings is provided in order to generate a three-dimensional angiography.

This may take place automatically; however, this is very difficult to implement in the angiography recordings or angiography images that are typically achieved. This is because even when the corresponding recording angle is chosen carefully, one or a number of superimpositions of coronary blood vessels or vessels of the body that are filled with contrast agent are present one below the other or of other objects or vessels of the body (e.g., of catheters and further anatomical structures with the vascular segment of the body to be examined). Since the angiography images are often low-contrast, image noise also plays an important role here.

On account of patient movements such as, for example, the breathing or a movement of a patient couch of a corresponding x-ray device, the at least two projection recordings or angiographic recordings, which are to be provided for the three-dimensional angiography, do not always belong spatially together and are to be adjusted or corrected accordingly (e.g., movement-corrected). This typically takes place via a shared reference point that is automatically offered in a software such as "IZ3D" by Siemens, for example, and is insensitive to distortions or vascular deformations between the two angiographic recordings of the vessel of the body. In such cases, the shared reference point may be adjusted manually.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a more precise two or three-dimensional angiography in a simple and convenient manner is obtained.

A method for segmenting a two-dimensional angiographic recording of a vessel of a body (e.g., a coronary blood vessel) by a computing apparatus is provided. The computing apparatus may be the computing apparatus of an x-ray device. For example, the vascular segment of the body may have a disease (e.g., a stenosis).

A first act involves providing a three-dimensional reconstruction of the vessel of the body on the computing apparatus. The three-dimensional reconstruction of the vessel of the body may be provided, for example, in the form of a recorded data record. The three-dimensional reconstruction of the vessel of the body may be a three-dimensional reconstruction of a first imaging or x-ray device (e.g., a computed tomography device or a magnetic resonance tomography device). A next act involves providing the two-dimensional angiographic recording of the vessel of the body on the computing apparatus. This provision of the two-dimensional angiographic recording may take place here in the form of providing an angiography data record. The two-dimensional angiographic recording of the vessel of the body may be the two-dimensional angiographic recording of a second x-ray device that differs from the first imaging device.

In a further act, the three-dimensional reconstruction of the vessel of the body or of the recorded data record of the three-dimensional reconstruction of the vessel of the body is registered at or with the two-dimensional recording of the vessel of the body or the angiography data record of the two-dimensional recording of the vessel of the body. The registration process is to be understood within an image registration, in which the three-dimensional reconstruction is related in a defined, clearly determined spatial relationship to the two-dimensional recording or the recorded data record with the angiography data record in a defined, clearly determined reference, in order to spatially match the vessel of the body in the three-dimensional reconstruction with the vessel of the body in the recorded angiography data record. Methods of automatic or semi-automatic image registration in three dimensions or two dimensions as well as mixtures of two- and three-dimensional data are known. On account of the registration, a transformation that, in a two-dimensional recording and three-dimensional reconstruction, assigns different regions or data that corresponds to the same object or object area or vascular area of the body to one another may thus be provided.

A next act involves projecting spatial information of the three-dimensional reconstruction onto the two-dimensional recording. The projection may take place, for example, at a predeterminable or predetermined angle, so that a virtual recording angle of the two-dimensional projection of the three-dimensional reconstruction onto the recording corresponds to a real recording angle of the two-dimensional recording of the vessel of the body. The predetermined angle may be, for example, a right angle or substantially a right angle. The two-dimensional recording may represent the vessel of the body in a heart phase, which corresponds or at least approximately corresponds to the heart phase of the vessel of the body, such as is shown in the reconstruction (e.g., with a predetermined maximum phase offset of at most 15 degrees).

A next act then involves segmenting the two-dimensional recording by using or as a function of the spatial information of the three-dimensional reconstruction projected onto the two-dimensional recording.

This is advantageous in that spatial information, which may easily be provided with the three-dimensional reconstruction or may be extracted herefrom, is used to segment the two-dimensional recording. The segmenting of the two-dimensional recording, which may generally only be realized with extreme difficulty, may thus be simplified. For example, the two-dimensional recording may thus be segmented automatically or fully automatically. The convenience but also the accuracy of the segmentation may thus also be improved. The quality of a three-dimensional angiography based on the two-dimensional recording may thus also be improved.

In an embodiment, the spatial information includes at least one centerline of the vessel of the body, which is projected onto the two-dimensional recording. For example, the centerline may likewise branch when the vessel of the body branches. The spatial information may also include a centerline of at least one further vessel of the body. A centerline for the vessel of the body is determined or defined on the recording based on or by using the projected centerline and is used in the segmentation. For example, the projected centerline of the vessel of the body may be determined as a centerline for the vessel of the body on the recording and may be used in the segmentation. By projecting the centerline from the three-dimensional reconstruction, an area to be segmented in the two-dimensional recording and/or a centerline in the two-dimensional recording is defined. Variations in the segmentation of the two-dimensional recording that may otherwise produce incorrect branchings when the two-dimensional recording is segmented may thus be identified and prevented, for example.

In a further embodiment, the spatial information includes segmentation information of the recorded data record of the three-dimensional reconstruction or segmentation information of the three-dimensional reconstruction of the vessel of the body. By projecting the segmentation information of the three-dimensional reconstruction into the two-dimensional recording, an edge detection (e.g., an automatic edge detection) of the vessel of the body may be assisted or refined in the two-dimensional recording. An automatic segmentation of the two-dimensional angiography may thus be realized or improved. A result of the segmentation is thus also easily and conveniently improved in this way, and if applicable, the accuracy of a subsequent three-dimensional angiography is increased.

In a further embodiment, the three-dimensional reconstruction includes or is a computed tomography and/or a magnetic resonance tomography. This is advantageous in that the three-dimensional reconstruction is particularly simple to segment and the segmentation of the two-dimensional recording is thus improved particularly easily. In practice, a computed tomography is already generated in many cases, so that an existing three-dimensional reconstruction and corresponding existing data or information may be accessed.

In a further embodiment, a variation between the spatial information projected onto the two-dimensional recording and an equivalent or corresponding information of the two-dimensional recording is detected prior to or during the use of the spatial information projected onto the two-dimensional recording. For example, a variation between a centerline of the vessel of the body, which is projected onto the two-dimensional recording, and a centerline that is determined for the vessel of the body on the recording may be detected, and/or a variation between the segmentation information of the three-dimensional reconstruction projected onto the two-dimensional recording and segmentation information that is determined for the two-dimensional recording may be detected. In such cases, the variation is also minimized by adjusting or correcting the two-dimensional recording. The two-dimensional recording may therefore be adjusted to the projection of the three-dimensional reconstruction. This adjustment may take place automatically.

This is advantageous in that spatial information of the three-dimensional reconstruction may be utilized or used particularly effectively for the segmentation and thus results in a particularly accurate result. In one embodiment, a further two-dimensional recording may be adjusted to the three-dimensional reconstruction, and thus, the one two-dimensional recording and the further two-dimensional recording may be adjusted indirectly to one another so that a three-dimensional angiography that, if applicable, subsequently takes place if necessary from both two-dimensional recordings is also improved.

The adjustment may include a displacement of the two-dimensional recording and/or rotation of the two-dimensional recording and/or a plastic deformation of the two-dimensional recording. A diameter of a vessel of the body is retained with the plastic deformation, for example. The displacement and/or rotation and/or plastic deformation may take place automatically, for example, by automatically minimizing the extent of the variation. The adjustment with the displacement and/or rotation and/or plastic deformation may thus include a further recording process (e.g., a fine tuning) of the equivalent information to the projected information. This is also advantageous in that the accuracy of the segmentation, a subsequent angiography generated from the two-dimensional recording, and a further two-dimensional recording that is likewise fine-tuned and/or deformed (e.g., adjusted) is increased.

In a further embodiment, a movement of the vessel of the body may be compensated by minimizing the variation. For example, the minimized variation may be a displacement of the vessel of the body caused by a breathing movement or by a couch movement and/or a geometric shortening of the vessel of the body or at least one area of the vessel of the body and/or another change caused by a breathing movement and/or by a couch movement. This is advantageous in that the previously conventional shared reference points, which always have to be manually adjusted, are omitted, and the corresponding motion correction of both two-dimensional recordings may thus also be performed automatically by adjusting the two-dimensional recording or two or more two-dimensional recordings to the three-dimensional reconstruction.

In a further embodiment, the provision, the registration, the projection, and the segmentation, in addition to implementation for the one two-dimensional angiographic recording, may be carried out in place of the one two-dimensional angiographic recording of the vessel of the body with the same two-dimensional reconstruction for a further two-dimensional angiographic recording of the vessel of the body. These acts are therefore carried out once with the one and then again with the other or further two-dimensional angiographic recording or recordings of the vessel of the body in each case. In such cases, the one angiographic recording with the further angiographic recording is suited to generating a three-dimensional angiography of the vessel of the body.

This is advantageous in that the individual angiographic recordings may profit from spatial information about the three-dimensional reconstruction and may be improved, and the two angiographic recordings may be improved in relation to one another (e.g., registered more accurately with one another). The accuracy of the three-dimensional angiography is thus increased. The method may also be carried out automatically or fully automatically.

In a further embodiment, a three-dimensional angiography of the vessel of the body may be generated from the two or more two-dimensional angiographic recordings by the computing apparatus. In such cases, the three-dimensional structure of the vessel of the body is adjusted in the three-dimensional angiography to a three-dimensional structure of the vessel of the body in the three-dimensional reconstruction. This is advantageous in that a faulty reconstruction of the three-dimensional structure of the vessel of the body in the three-dimensional angiography may be easily compensated or corrected. An improved three-dimensional angiography may thus also take place automatically, for example.

One or more of the present embodiments also relate to an examination system for segmenting a two-dimensional angiographic recording of a vessel of a body. The examination system includes a medical imaging device for providing a three-dimensional reconstruction of the vessel of the body (e.g., a computed tomograph) and an angiography device for providing the two-dimensional angiographic recording of the vessel of the body. The examination system also includes a computing apparatus that may be coupled to the medical imaging device. In such cases, the computing apparatus is configured to register the three-dimensional reconstruction of the vessel of the body with the two-dimensional recording of the vessel of the body and to project spatial information of the three-dimensional reconstruction onto the two-dimensional recording. The computing apparatus is also configured to segment the two-dimensional recording by using the spatial information projected onto the two-dimensional recording.

Advantages and advantageous embodiments of the examination system correspond to the advantages and advantageous embodiments of the method.

The features and combinations of features mentioned in the description above and the following features and combinations of features cited below in the description of the drawings and/or shown in the drawing alone are usable not only in the respective combination given, but also in other combinations without departing from the scope of the invention. Embodiments of the invention that are not explicitly shown in the figures and described, but arise and may be created through separate combinations of features from the embodiments described may therefore also be considered to be included and disclosed. Explanations and combinations of features that therefore do not have all features of an originally formulated independent claim are also to be regarded as disclosed. Embodiments and combinations of features (e.g., by the embodiments disclosed above) that go beyond or deviate from the combinations of features represented by the references in the claims are to be regarded as disclosed.

BRIEF DESCRIPTION OF THE DRAWINGS

FIG. 1 shows a schematic flow diagram of an exemplary method for segmenting a two-dimensional angiographic recording of a vessel of a body.

DETAILED DESCRIPTION

In a first act 1, a three-dimensional reconstruction of a vessel of a body (e.g., a coronary blood vessel) is provided. A three-dimensional reconstruction is provided in the form of a recorded data record. The recorded data record is produced by a first imaging device (e.g., a computed tomography (CT) device). A next act 2 involves further providing a first two-dimensional angiographic recording of the coronary blood vessel of a further imaging device (e.g., an x-ray device). This further provision 2 also takes place on the computing apparatus (e.g., in the form of an angiography data record).

In the example shown, the recorded data record and thus the three-dimensional reconstruction of the vessel of the body are thus registered 3 with the angiography data record, and thus, the two-dimensional recording of the vessel of the body that is present, for example, as a coronary blood vessel. This is followed by projecting 4 spatial information of the three-dimensional reconstruction (e.g., a number of centerlines of the coronary heart vessel) onto the two-dimensional recording. The projection 4 is carried out with a right angle as a projection angle, so that the projected spatial information of the three-dimensional reconstruction (e.g., the projected centerlines of the coronary heart vessel) and the two-dimensional recording may be placed one above the other, and accordingly, using the spatial information of the three-dimensional reconstruction, the centerlines, centerlines may be defined for the coronary blood vessel on the two-dimensional recording, for example. The projected centerlines may be taken over for the recording, for example, or an algorithm for finding at least one centerline may consider or use the projected centerlines. This may, however, be omitted in the currently described example.

A next act is then a segmentation 5 of the two-dimensional recording using the spatial information (e.g., the centerlines) projected onto the two-dimensional recording. The projected centerline or a centerline derived from the projected centerline may therefore currently also be considered or included in the segmentation, for example. Incorrect branchings, which often occur with a conventional segmentation of a two-dimensional recording, may thus be identified and prevented with the aid of the projected spatial information (e.g., the centerlines).

The segmentation 5 currently also includes detecting 6 a variation between the spatial information projected onto the two-dimensional recording (e.g., the centerlines) and corresponding information (e.g., the centerlines of the two-dimensional recording), which are first determined in the segmented two-dimensional recording. The variation between the projected centerlines and the centerlines determined in the two-dimensional recording is minimized in the example shown by adjusting the two-dimensional recording. Using the adjustment, the two-dimensional recording is currently displaced and rotated until the projected spatial information matches the corresponding information from the two-dimensional recording (e.g., the projected centerline and the centerline determined in the segmented two-dimensional recording coincide). Alternatively or in addition, a deformation of the two-dimensional recording may also be provided.

In the example shown, the provision 2, the registration 3, the projection 4 and the segmentation 5 including the detection 6 are additionally carried out for a further two-dimensional angiographic recording of the vessel of the body shown as a coronary blood vessel. In such cases, both two-dimensional angiographic recordings are suited for generating 7 a three-dimensional angiography of the vessel of the body shown as a coronary blood vessel (e.g., to assign corresponding recording angles that are at a minimum differential angle from one another).

In the example shown, in a further act, after segmenting 6 the further two-dimensional angiographic recording, the computing apparatus generates 7 the three-dimensional angiography of the vessel of the body (e.g., the coronary blood vessel) from both two-dimensional angiographic recordings. This three-dimensional angiography is particularly accurate here, since the individual angiographic two-dimensional recordings already have an improved accuracy on account of the spatial information relating to the three-dimensional reconstruction that is utilized or used. The adjustment with the displacement and rotation and, if applicable, deformation of the two-dimensional recordings corresponds, for example, to an indirect registration of both two-dimensional recordings to one another, which likewise results in an improved three-dimensional angiography.

In the example shown after the production act 7, an adjustment 8 of the three-dimensional structure of the vessel of the body in the three-dimensional angiography to a three-dimensional structure of the vessel of the body in the three-dimensional reconstruction is provided again as a further act in the example shown for a further improvement to the three-dimensional angiography. Faulty reconstructions and precisely faulty reconstructions that refer back to a geometric shortening in the two-dimensional recordings may be immediately identified and compensated. This applies precisely to areas of the vessel of the body that are arranged at a distance from a stenosis area, which is typically detected very accurately by the two-dimensional angiographic recordings. A corresponding faulty reconstruction may thus be compensated, for example, by combining the different information or data in the three-dimensional angiography.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for segmenting a two-dimensional angiographic recording of a vessel of a body by a computing apparatus, the method comprising:
   providing a three-dimensional reconstruction of the vessel of the body on the computing apparatus;
   providing the two-dimensional angiographic recording of the vessel of the body on the computing apparatus;
   registering the three-dimensional reconstruction of the vessel of the body with the two-dimensional angiographic recording of the vessel of the body;
   projecting spatial information of the three-dimensional reconstruction onto the two-dimensional angiographic recording, the projecting comprising detecting a variation between the spatial information of the three-dimensional reconstruction and corresponding spatial information of the two-dimensional angiographic recording and adjusting the two-dimensional angiographic recording based on the variation; and segmenting the two-dimensional angiographic recording using the spatial information projected onto the two-dimensional angiographic recording, wherein the adjusting comprises displacing, rotating, or displacing and rotating the two-dimensional angiographic recording, deforming the two-dimensional angiographic recording, or a combination thereof.

2. The method of claim 1, wherein the spatial information comprises at least one centerline of the vessel of the body that is projected onto the two-dimensional angiographic recording, and based on the at least one projected centerline, a centerline for the vessel of the body is determined on the two-dimensional angiographic recording and is used in the segmentation.

3. The method of claim 2, wherein the at least one projected centerline is determined as a centerline for the vessel of the body on the recording and is used in the segmentation.

4. The method of claim 1, wherein the spatial information comprises segmentation information of the three-dimensional reconstruction of the vessel of the body.

5. The method of claim 1, wherein the three-dimensional reconstruction comprises a computed tomography or a magnetic resonance tomography.

6. The method of claim 1, further comprising:
minimizing the variation, the minimizing comprising adjusting the two-dimensional angiographic recordings,
wherein the detecting is prior to or during use of the spatial information projected onto the two-dimensional angiographic recording.

7. The method of claim 6,
wherein a diameter of the vessel of the body is retained.

8. The method of claim 7, wherein a diameter of the vessel of the body is retained with a plastic deformation.

9. The method of claim 6, wherein the variation is minimized, such that a movement of the vessel of the body is compensated.

10. The method of claim 9, wherein the variation is minimized, such that a displacement of the vessel of the body caused by a breathing movement, a couch movement, a geometric shortening of the vessel of the body caused by a movement, or any combination thereof is compensated.

11. The method of claim 1, wherein the providing of the two-dimensional angiographic recording of the vessel, the registering, the projecting, and the segmenting are additionally carried out for one or more further two-dimensional angiographic recordings of the vessel of the body in place of the two-dimensional angiographic recording of the vessel of the body with the same three-dimensional reconstruction.

12. The method of claim 11, further comprising:
generating a three-dimensional angiography of the vessel of the body from the two-dimensional angiographic recording and the one or more further two-dimensional angiographic recordings by the computing apparatus; and adjusting a three-dimensional structure of the vessel of the body in the three-dimensional angiography to a three-dimensional structure of the vessel of the body in the three-dimensional reconstruction.

13. The method of claim 1, wherein the variation is minimized by adjusting the two-dimensional angiographic recording.

14. An examination system for segmenting a two-dimensional angiographic recording of a vessel of a body, the examination system comprising:
a medical imaging device configured to provide a three-dimensional reconstruction of the vessel of the body;
an angiography device configured to provide the two-dimensional angiographic recording of the vessel of the body; and
a computer that is coupleable to the medical imaging device, the computing apparatus being configured to:
register the three-dimensional reconstruction of the vessel of the body with the two-dimensional angiographic recording of the vessel of the body;
project spatial information of the three-dimensional reconstruction onto the two-dimensional angiographic recording;
detect a variation between the spatial information of the three-dimensional reconstruction and corresponding spatial information of the two-dimensional angiographic recording;
adjust the two-dimensional angiographic recording based on the variation; and
segment the two-dimensional angiographic recording using the spatial information projected onto the two-dimensional angiographic recording,
wherein adjusting the two-dimensional angiographic recording comprises displacing, rotating, or displacing and rotating the two-dimensional angiographic recording, deforming the two-dimensional angiographic recording, or a combination thereof.

15. The examination system of claim 14, wherein the medical imaging device comprises a computed tomography (CT) device.

16. The examination system of claim 14, wherein the spatial information comprises at least one centerline of the vessel of the body that is projected onto the two-dimensional angiographic recording, and
wherein the computer is configured to determine, based on the at least one projected centerline, a centerline for the vessel of the body on the two-dimensional angiographic recording and is configured to use the centerline for the vessel of the body in the segmentation.

17. The examination system of claim 16, wherein the at least one projected centerline is determined as a centerline for the vessel of the body on the recording and is used in the segmentation.

18. The examination system of claim 14, wherein the spatial information comprises segmentation information of the three-dimensional reconstruction of the vessel of the body.

19. The examination system of claim 14, wherein the computer is configured to minimize the variation, the minimization of the variation comprising adjustment of the two-dimensional angiographic recording.

* * * * *